US007959595B2

(12) United States Patent
Melsheimer et al.

(10) Patent No.: US 7,959,595 B2
(45) Date of Patent: Jun. 14, 2011

(54) CATHETER ASSEMBLY

(75) Inventors: Jeffry S. Melsheimer, Springville, IN (US); Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 287 days.

(21) Appl. No.: 11/857,060

(22) Filed: Sep. 18, 2007

(65) Prior Publication Data
US 2009/0076435 A1  Mar. 19, 2009

(51) Int. Cl.
*A61M 37/00* (2006.01)
(52) U.S. Cl. ............... 604/6.16; 604/4.01; 604/5.01; 604/6.1; 604/8; 604/96.01
(58) Field of Classification Search ............ 604/4, 5, 604/6, 8, 96
See application file for complete search history.

(56) References Cited

U.S. PATENT DOCUMENTS

| | | | | |
|---|---|---|---|---|
| 3,094,122 A | | 6/1963 | Gauthier et al. | 123/221 |
| 3,204,634 A | | 9/1965 | Koehn | 128/214 |
| 3,993,079 A | | 11/1976 | Henriques de Gatztañondo | 128/347 |
| 4,134,402 A | * | 1/1979 | Mahurkar | 604/44 |
| 4,240,833 A | * | 12/1980 | Myles | 501/4 |
| 4,535,773 A | * | 8/1985 | Yoon | 606/185 |
| 4,767,407 A | | 8/1988 | Foran | 604/164 |
| 4,772,268 A | * | 9/1988 | Bates | 604/174 |
| 5,106,368 A | * | 4/1992 | Uldall et al. | 604/43 |
| 5,221,255 A | * | 6/1993 | Mahurkar et al. | 604/43 |
| 5,306,239 A | | 4/1994 | Gurmarnik et al. | 604/51 |
| 5,328,480 A | | 7/1994 | Melker et al. | 604/164 |
| 5,549,564 A | * | 8/1996 | Yoon | 604/164.12 |
| 5,573,510 A | | 11/1996 | Isaacson | 604/158 |
| 5,674,240 A | | 10/1997 | Bonutti et al. | 606/198 |
| 5,733,266 A | * | 3/1998 | Gravlee, Jr. | 604/272 |
| 5,735,813 A | | 4/1998 | Lewis | 604/43 |
| 5,893,844 A | | 4/1999 | Misawa | 604/195 |
| 6,391,007 B2 | | 5/2002 | Chang et al. | 604/164.01 |
| 6,398,743 B1 | | 6/2002 | Halseth et al. | 600/585 |
| 6,921,386 B2 | | 7/2005 | Shue et al. | 604/164.01 |
| 7,153,276 B2 | * | 12/2006 | Barker et al. | 600/576 |
| 7,608,063 B2 | * | 10/2009 | Le et al. | 604/264 |
| 2002/0065492 A1 | | 5/2002 | McGuckin, Jr. et al. | 604/264 |

OTHER PUBLICATIONS

Palmer, Robert M. Cull, et al., "*Is Surgical Thrombectomy to Salvage Failed Autogenous Arteriovenous Fistulae Worthwhile?*"; The American Surgeon, Dec. 2006, vol. 72, pp. 1231-1233.
Van Tricht, Ilse, et al., "*Hemodynamics and Complications Encountered with Arteriovenous Fistulas and Grafts as Vascular Access for Hemodialysis: A Review*"; Annals of Biomedical Engineering, vol. 33, No. 9, Sep. 2005, pp. 1142-1157.

(Continued)

*Primary Examiner* — Tatyana Zalukaeva
*Assistant Examiner* — Ilya Y Treyger
(74) *Attorney, Agent, or Firm* — Brinks Hofer Gilson & Lione

(57) ABSTRACT

A catheter assembly is provided with a flexible tubular body having two lumens. A solid slidable member with a sharp distal end is disposed within one of the lumens. The slidable member is capable of sliding within the lumen of the tubular body between an exposed position in which the sharp distal end of the slidable member protrudes from the distal end of the tubular body and a shielded position in which the distal end of the slidable member is within the tubular body. One advantage is that the sharp distal end of the slidable member may be withdrawn into the tubular body in order to shield a patient from unintentional cutting or irritation from the sharp distal end of the slidable member.

3 Claims, 9 Drawing Sheets

OTHER PUBLICATIONS

Malberti, Fabio, *Correspondence: "More Infiltration in Less Mature Fistulae?"*; American Journal of Kidney Diseases, vol. 48, No. 1, Jul. 2006, pp. 181-182.

Schwab, Steve J., *"Improving Access Patency: Pre-End-Stage Renal Disease Strategies"*; J. Am. Soc. Nephrol., vol. 9, 1998, pp. S124-S129.

Konner, Klaus, *Invited Comment: "A Primer on the Av Fistula-Achilles' Heel, But Also Cinderella of Haemodialysis"*; Nephrol. Dial Transplant, 1999, 14: pp. 2094-2098.

Swartz, Richard D., et al., *"Successful Use of Cuffed Central Venous Hemodialysis Catheters Inserted Percutaneously"*; J. Am. Soc. Nephrol., 1994; pp. 4:1719-1725.

* cited by examiner

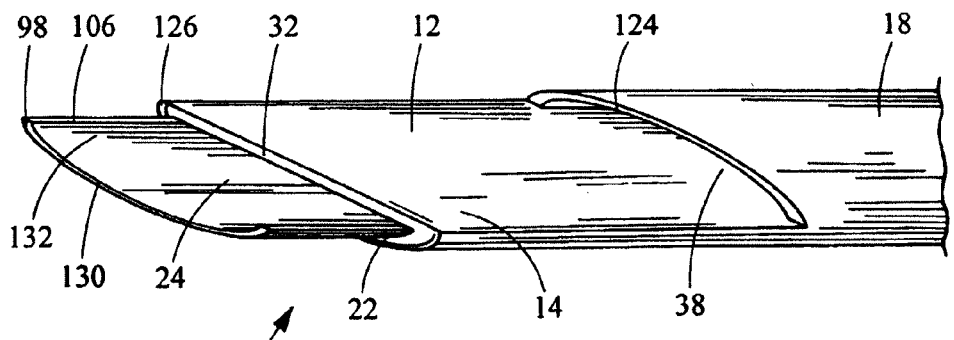
Fig. 9
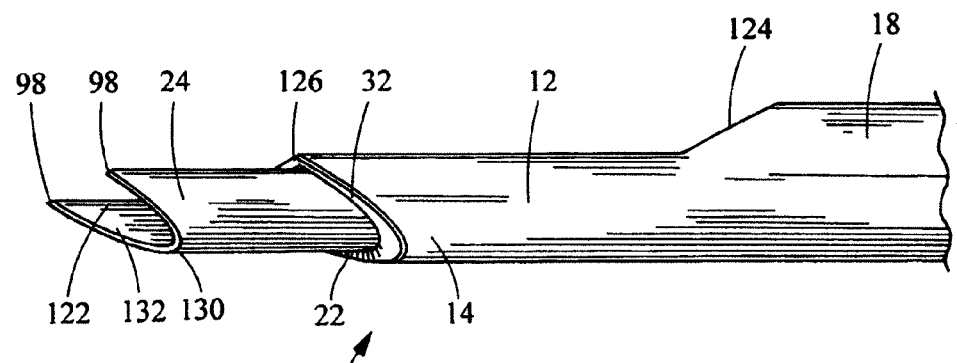
Fig. 10
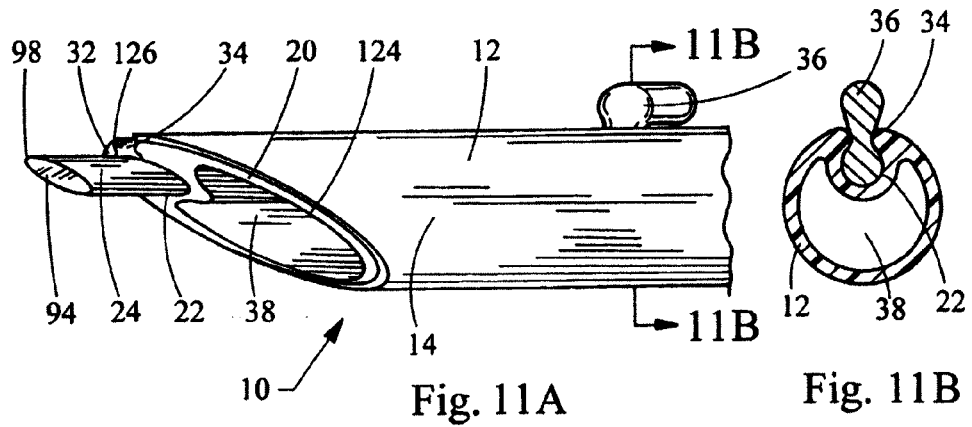
Fig. 11A
Fig. 11B

CATHETER ASSEMBLY

BACKGROUND

The present invention relates generally to medical devices and more particularly to devices for accessing a lumen inside a body.

One type of minimally invasive medical procedure is hemodialysis. Hemodialysis is the most common treatment for permanent or chronic kidney failure. Kidney failure results in the body's inability to filter toxins, fluids, and waste from the blood, resulting in a potentially life-threatening build-up of these substances. Among the substances that often build up as a result of kidney failure are urea, potassium, and phosphates. When undergoing hemodialysis, a person suffering from kidney failure utilizes a machine to perform the filtering function normally performed by the kidneys.

Persons requiring hemodialysis generally must use a dialysis machine for several hours at a time. Treatment must occur several days each week. During treatment, a needle typically is used to draw blood, usually from an artery. The blood is run through the dialysis machine, which filters out harmful toxins, excess fluids, and wastes. The filtered blood is then returned to the body via a second needle inserted at a different point in the vascular system, preferably a vein. Blood must be drawn from a vessel with a high rate of flow because the dialysis machine processes blood at a high rate of speed. Using a vessel with an insufficient rate of blood flow may cause the vessel to collapse as the dialysis machine draws blood out of the body.

In order to insure that a high blood flow rate is present, blood is often drawn from an arteriovenous (AV) fistula. AV fistulas include autogenous fistulas, which are composed of naturally occurring blood vessels, and non-autogenous fistulas, which are made of synthetic materials or non-native blood vessels. An autogenous fistula consists of an artery and a vein that are directly connected together, allowing blood to bypass smaller capillaries. Fistulas are most often surgically created in the arm, but may be created elsewhere in the body. Blood flow through a fistula is generally greater than the blood flow through a naturally occurring artery or vein, maximizing the amount of blood that may be filtered by the dialysis machine in a period of time. Non-autogenous fistulas are created by using an artificial graft of biocompatible tubing or a non-native blood vessel to create a high blood flow vascular access site. Non-autogenous fistulas are commonly referred to as "grafts." Common materials used for non-autogenous fistulas (grafts) include polytetrafluorethylene (PTFE), silicone, and biologic materials. For example, a graft may be created using a natural vessel harvested from another part of the body, such as the leg, and used to connect an artery and a vein together in a patient's arm. Alternatively, a bovine or sheep vessel may be utilized. After they are surgically connected, both autogenous fistulas and non-autogenous fistulas (grafts) take several weeks to mature to the point that the vascular access site can be used for hemodialysis. Once mature, a needle for withdrawing blood is typically inserted in the arterial side of vascular access site and a needle for returning the filtered blood is inserted into the venous side of the vascular access site.

A patient without a mature vascular access site may utilize central venous hemodialysis. In this type of hemodialysis, blood is drawn from a large blood vessel in the chest or neck such as the vena cava, internal jugular vein, subclavian vein, or femoral vein. For central venous hemodialysis, a single plastic catheter with two lumens is typically used. This type of hemodialysis allows less blood flow than a fistula. It is also associated with a high rate of infection.

In most forms of hemodialysis, due to the large amount of blood that is removed, two large hypodermic needles are typically used. One needle is used to withdraw blood, while the second is used to return the blood to the body. These needles must remain in place for hours at a time and they must be used multiple times weekly, often for years. The needles normally must remain inside the blood vessel for long periods of time, during which time the patient may move or shift positions, causing the needle to irritate the blood vessel walls. Irritation from the needles may cause scar tissue to form within the lumen of the blood vessel or fistula. Over time, scar tissue may build up, narrowing the blood vessel or fistula. This narrowing of the vascular system may also be referred to as a stenosis. Stenosis of a blood vessel or fistula may result in thrombosis, i.e., clotting of the blood vessels. Thrombosis may render a particular blood vessel or fistula unusable. The repeated use of needles to penetrate the vessel or fistula may also weaken the vascular access site, causing aneurysms and pseudoaneurysms. An aneurysm is an abnormal blood-filled dilation of a blood vessel. A pseudoaneurysm is an abnormal twisting or pouching of a blood vessel that resembles a true aneurysm in appearance. Blood slows and collects in aneurysms and pseudoaneurysms, increasing the risk that it will coagulate and result in thrombosis.

Stenosis, aneurysms, and pseudoaneurysms, and the resulting thrombosis, can reduce the longevity of a vascular access site. When a vascular access site becomes unusable, a patient must choose between having a doctor surgically thrombectomize the vascular access site to clear the thrombosis or using an alternate site. Studies have shown that over 70% of vascular access sites that are thrombectomized become clotted again within six months. Because of the high rate of reoccurrence, when a fistula becomes unusable, patients often must switch to central venous hemodialysis until a new fistula can be surgically created and has matured. These surgeries are expensive and time consuming. In addition, with every surgery, patients undergo a risk of infection and other potentially life-threatening complications.

BRIEF SUMMARY

A catheter assembly having a catheter with at least two lumens is described. A solid, slidable member with a sharp distal end is disposed within the first lumen. The sharp distal end of the slidable member may be used to puncture the skin and insert the catheter assembly into a vein, artery, or fistula. The slidable member may then be moved in relation to the distal end of the catheter so that it is withdrawn into the first lumen. One advantage of the ability of the slidable member to be withdrawn is that it prevents the sharp distal end of the slidable member from contacting the interior wall of the blood vessel during hemodialysis, thereby reducing the risk of lacerating or irritating the blood vessel or fistula. Blood may flow either into or from a dialysis machine through a second lumen of the catheter as desired.

The invention may include any of the following aspects in various combinations and may also include any other aspect described below in the written description or in the attached drawings.

A catheter assembly comprising:

a flexible tubular body comprising a distal end, a proximal end, and an elongate center portion between the distal end and the proximal end;

a beveled edge at the distal end of the tubular body;

a first lumen running longitudinally from the distal end of the tubular body to the proximal end of the tubular body;

a second lumen adjacent the first lumen; and a solid slidable member disposed within the first lumen, the slidable member having a distal end, a proximal end, and an elongate center portion between the distal end and the proximal end, the distal end of the slidable member being capable of cutting through skin, the slidable member being capable of moving between an exposed position in which the distal end of the slidable member is located distally from the distal end of the tubular body and a shielded position in which the distal end of the slidable member is located proximally from the distal end of the tubular body.

The catheter assembly, wherein the elongate center portion of the slidable member is cylindrical.

The catheter assembly, wherein the second lumen has a crescent-like cross-sectional shape wrapped around the first lumen.

The catheter assembly, wherein the distal end of the slidable member comprises at least three faces, the at least three faces forming a point at the most distal location of the distal end of the slidable member.

The catheter assembly, wherein the slidable member has a non-circular cross-sectional shape.

The catheter assembly, wherein the slidable member is curved such that the slidable member has a crescent-like cross-sectional shape.

The catheter assembly, wherein the second lumen has a circular cross-sectional shape.

The catheter assembly, wherein a hub is attached about the proximal end of the tubular body.

The catheter assembly further comprising:

a slot in the tubular body along the first lumen;

a sliding mechanism connected to the slidable member, the sliding mechanism protruding through the slot such that the sliding mechanism may be used to control the sliding of the slidable member between the exposed position and the shielded position.

The catheter assembly, wherein a hub is attached about the proximal end of the tubular body, the hub being connected to the sliding mechanism thereby allowing a user to operate the sliding mechanism with the hub.

The catheter assembly, wherein each of the first and second lumens comprises a distal end and a proximal end, the distal end of the first lumen being located distally from the distal end of the second lumen, the distal end of the tubular body being tapered such that the distal end of the first lumen comprises the narrowest portion of the tapered distal end of the tubular body and the distal end of the second lumen is located proximally to the narrowest portion of the tapered distal end of the tubular body.

A catheter assembly comprising:

a tubular body having a distal end and a proximal end, the tubular body having a first lumen and a second adjacent lumen, each of the first and the second lumens comprising a distal end and a proximal end;

a solid slidable member disposed within the first lumen, the slidable member not completely occupying the first lumen, the slidable member having a distal end capable of cutting through skin and the slidable member being capable of moving between an exposed position in which the distal end of the slidable member is located distally from the distal end of the tubular body and a shielded position in which the distal end of the slidable member is located proximally from the distal end of the tubular body.

The catheter assembly further comprising:

a first beveled edge located at the distal end of the first lumen;

a second beveled edge located at the distal end of the second lumen, the first beveled edge and the second beveled edge together forming a single beveled edge at the distal end of the tubular body.

The catheter assembly further comprising:

a first beveled edge located at the distal end of the first lumen;

a second beveled edge located at the distal end of the second lumen, the first beveled edge being located distally from the second beveled edge.

The catheter assembly, wherein the distal end of the first lumen is located distally from the distal end of the second lumen, the distal end of the tubular body being tapered such that the distal end of the first lumen comprises the narrowest portion of the tapered distal end of the tubular body and the distal end of the second lumen is located proximally to the narrowest portion of the tapered distal end of the tubular body.

The catheter assembly, wherein a hub is attached about the proximal end of the tubular body.

The catheter assembly further comprising:

a slot in the tubular body along the first lumen;

a sliding mechanism thereby allowing the slidable member to slide between the exposed position and the shielded position, wherein the sliding mechanism protrudes through the slot such that the sliding mechanism may be used to control the sliding of the slidable member.

A catheter assembly comprising:

a catheter having a distal end and a proximal end;

a lumen running longitudinally from the distal end of the catheter to the proximal end of the catheter; and a solid slidable member disposed within the lumen, the slidable member having an elongate center portion, the elongate center portion having a proximal end and a distal end, the slidable member being adapted to slide within the first lumen;

an expandable tip attached to the distal end of the elongate center portion of the slidable member, the tip of the slidable member comprising a first leg and a second leg, wherein the first leg extends from the distal end of the elongate center portion to a most distal location of the slidable member and the second leg is attached to the most distal location and extends proximally therefrom, the second leg being curved and forming a cutting surface capable of cutting skin, wherein the second leg engages the opening of the lumen when the slidable member is retracted within the lumen, thereby compressing the second leg to permit the expandable tip of the slidable member to be withdrawn into the lumen.

The catheter assembly, wherein the second leg has a distal end and a proximal end and the proximal end of the second leg is connected to the distal end of the elongate center portion of the slidable member.

The catheter assembly, wherein the second leg has a distal end and a proximal end and the proximal end of the second leg is unconnected to the elongate center portion of the slidable member.

BRIEF DESCRIPTION OF THE DRAWINGS

FIG. 9 is a partial perspective view of a catheter assembly;

FIG. 10 is a partial perspective view of a catheter assembly;

FIG. 11A is a partial perspective view of a catheter assembly;

FIG. 11B is a cross-sectional view of the catheter assembly of FIG. 11A taken along line 11B-11B;

DETAILED DESCRIPTION OF THE DRAWINGS AND THE PRESENTLY PREFERRED EMBODIMENTS

Figure 1A:
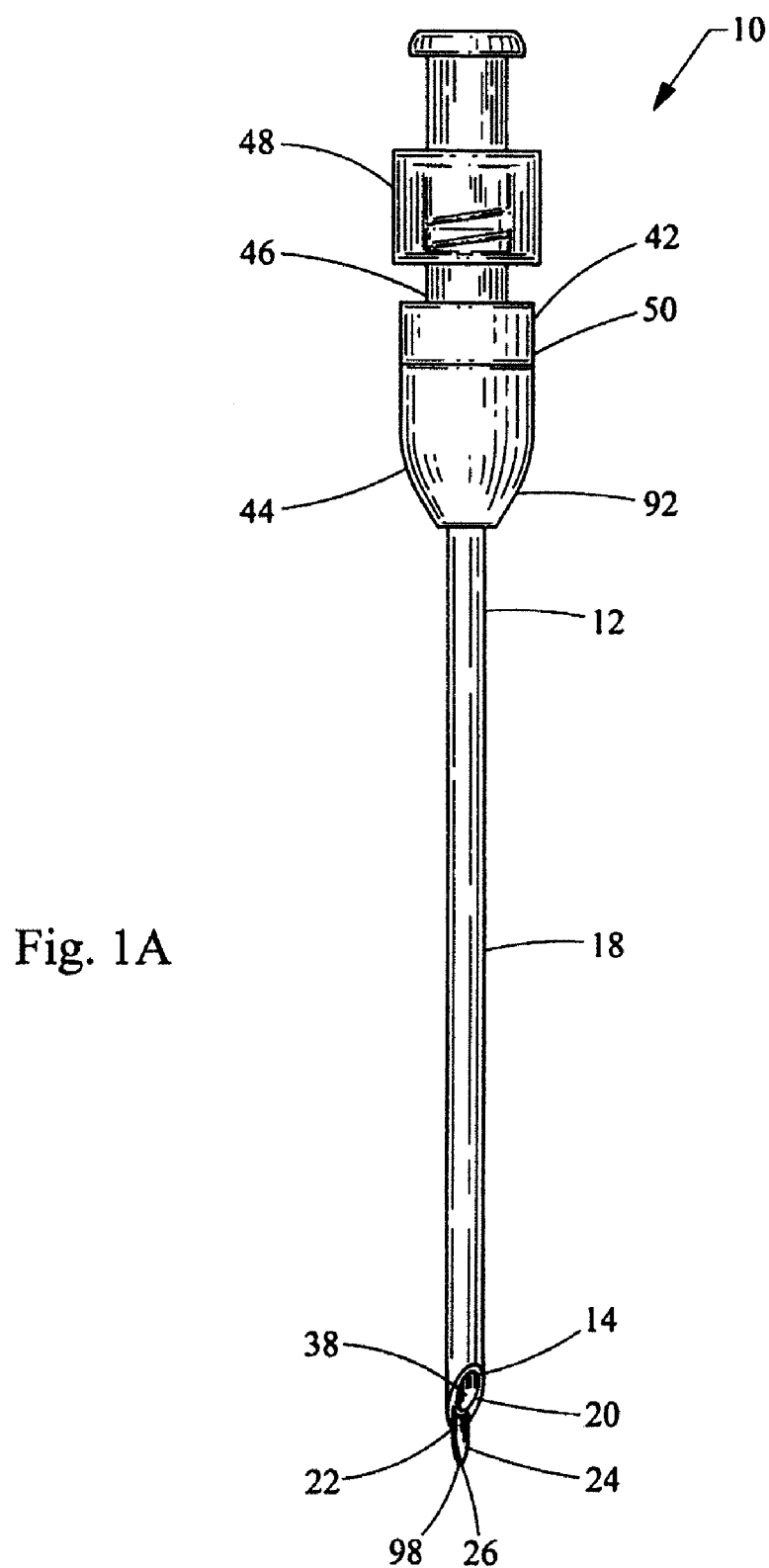
FIG. 1A is a perspective view of a catheter assembly.

Referring now to the drawings, and particularly to FIG. 1A, a catheter assembly 10 is shown. The catheter assembly 10 includes a flexible tubular body 12 with a distal end 14 and a proximal end. An elongate center portion 18 of the tubular body 12 is located between the distal end 14 and the proximal end 16 of the tubular body 12. The embodiment shown in FIG. 1A has a beveled edge 20 located at the distal end 14 of the tubular body 12. The tubular body 12 contains two adjacent lumens running longitudinally between the distal end 14 and the proximal end of the tubular body 12. The first lumen 22 houses a slidable member 24 that is capable of sliding within the first lumen 22. The slidable member 24 has a distal end 26, a proximal end 28, and an elongate center portion 30.

Figure 1B:
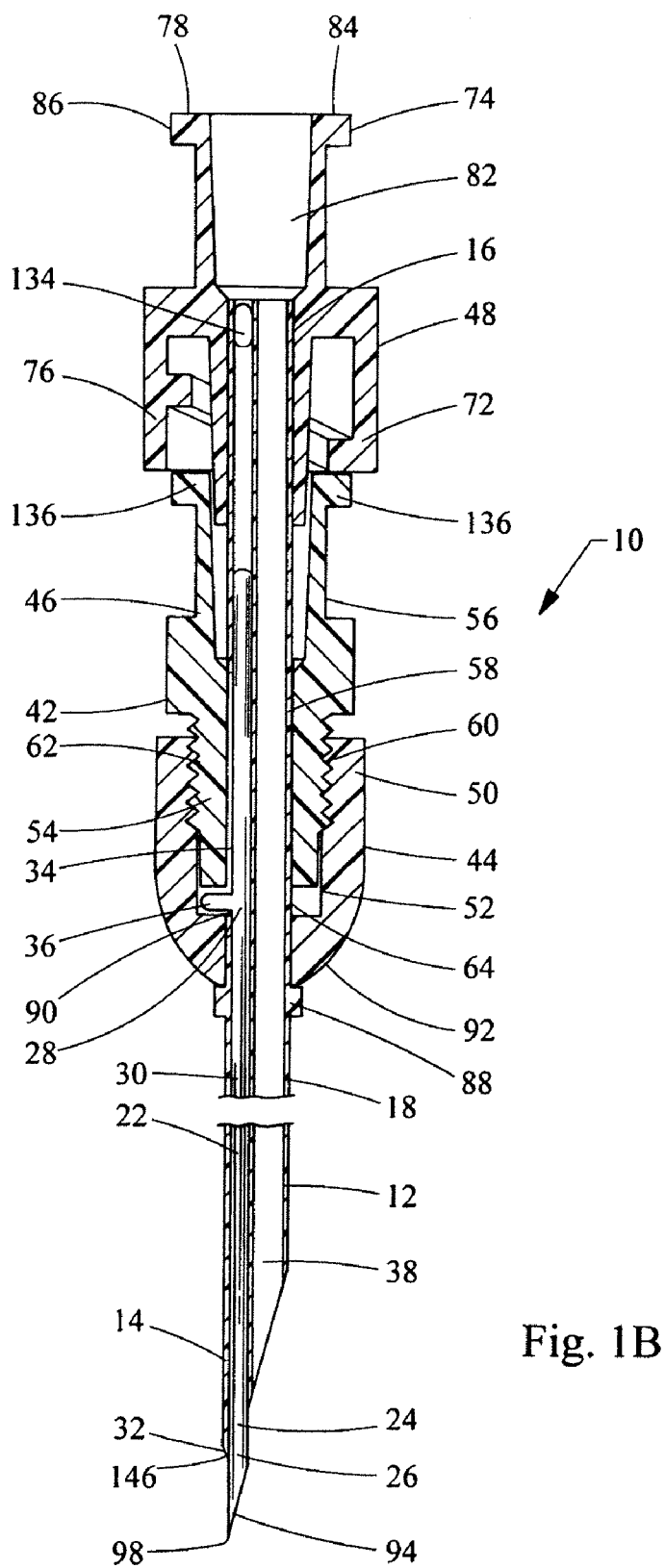
FIG. 1B is a cross-sectional view of a catheter assembly.
Figure 1C:
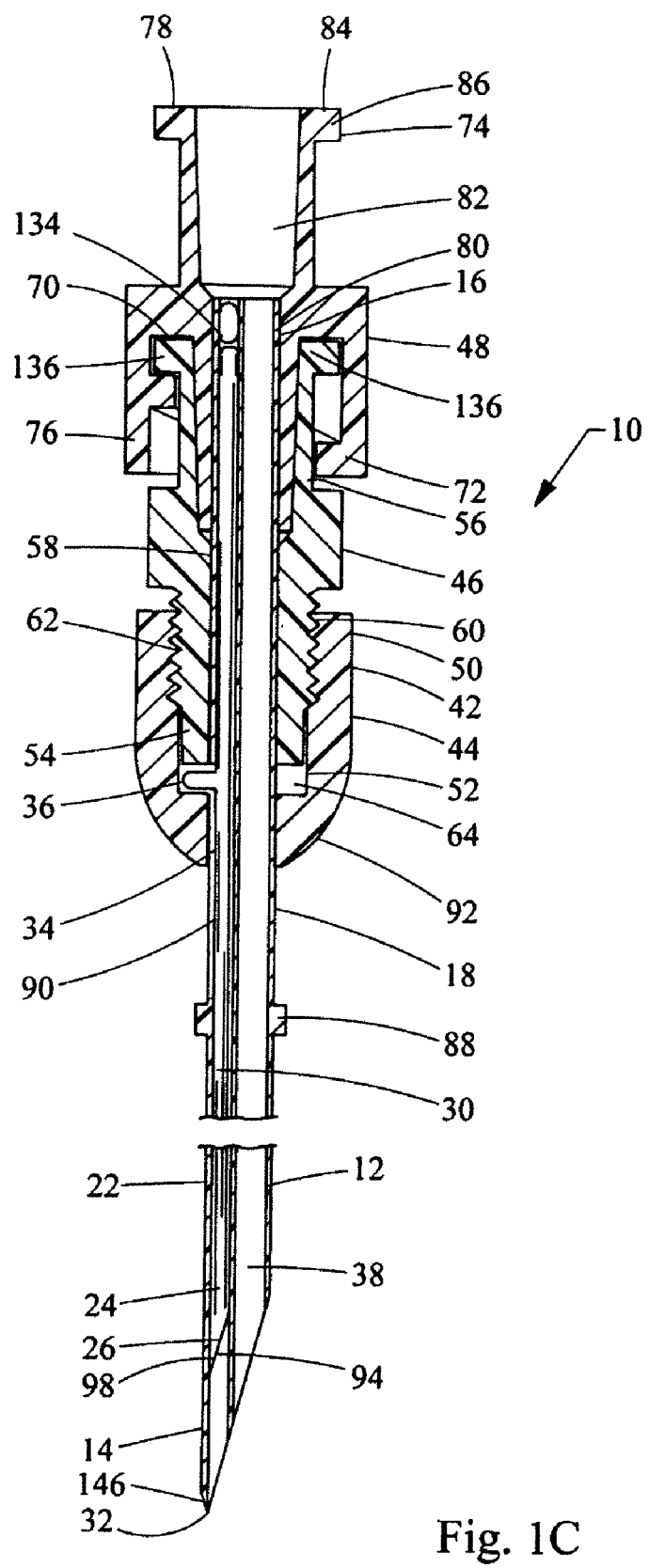
FIG. 1C is a cross-sectional view of a catheter assembly.

FIGS. 1B and 1C illustrate that the slidable member 24 may move within the first lumen 22 of the catheter assembly 10 shown in FIG. 1A between a shielded position and an exposed position. FIG. 1B shows the slidable member 24 in an exposed position. In the exposed position, the slidable member 24 is situated within the first lumen 22 so that the distal end 26 of the slidable member 24 protrudes from the distal end 32 of the first lumen 22 of the tubular body 12. As shown in FIG. 1C, the slidable member 24 may also be placed in a shielded position in which the slidable member is positioned so that the distal end 26 of the slidable member 24 is located proximally from the distal end 14 of the tubular body 12. In some embodiments, the slidable member 24 may be withdrawn into the tubular body 12. It is preferable that the slidable member 24 is only capable of moving a limited distance longitudinally in relation to the tubular body 12.

Figure 2:
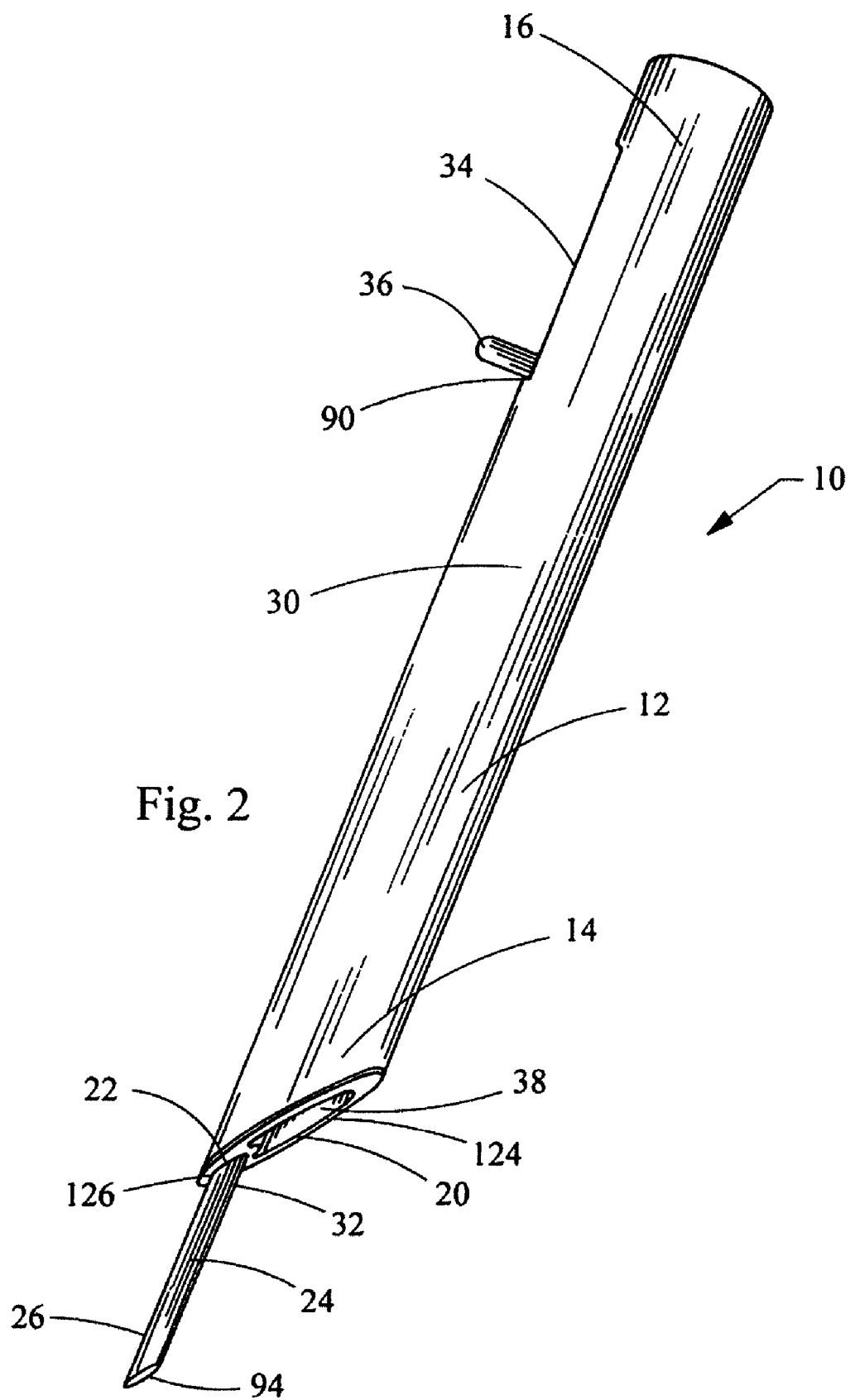
FIG. 2 is a perspective view of a catheter assembly.

In the embodiment shown in FIG. 2, the sliding of the slidable member 24 is facilitated by a slot 34 in the tubular body 12, which houses a knob 36. The slot 34 preferably runs longitudinally and is located along the length of the first lumen 22. The knob 36 is preferably attached to the slidable member 24. The user may grasp the knob 36 and move it in the distal direction to slide the slidable member 24 distally and into the exposed position. Conversely, the user may move the knob 36 in the proximal direction to slide the slidable member 24 proximally and into the shielded position. Other embodiments may use an arm of the slidable member 24, an extension of the slidable member 24, a handle, a lever, a grip, or any other sliding mechanism known to a person of ordinary skill in the art in place of a knob 36. Still other embodiments do not have a slot 34 or a sliding mechanism at all.

The catheter assembly 10 is useful for accessing a lumen inside a body and is particularly well-suited for accessing the lumen of a blood vessel. One use of the catheter assembly 10 is to provide vascular access for a hemodialysis patient. When using the catheter assembly 10 for hemodialysis, a user first places the slidable member 24 in the exposed position. The user then punctures the skin and the desired blood vessel or fistula by pushing the catheter assembly 10 through the skin and underlying tissue and into the desired point in the vasculature. The sharp distal end 26 of the slidable member 24 facilitates cutting the skin and the underlying tissue. Once the distal end 14 of the tubular body 12 is positioned within the lumen of the desired blood vessel or fistula the user moves the slidable member 24 into the shielded position. During hemodialysis, the interior walls of the blood vessel or fistula are shielded from contact with the sharp distal end of the slidable member 24 by the flexible tubular body 12. This feature reduces the risk of damaging the blood vessel or fistula during the course of hemodialysis, thereby also reducing the risk of stenosis, thrombosis, aneurysms, and pseudoaneurysms. This is particularly useful in hemodialysis because of the long duration of hemodialysis procedures, the repetitive need for treatment, and the large, sharp needles typically used that exacerbate the risk of damaging the vasculature.

For many types of hemodialysis treatment, a second catheter assembly 10 may be inserted in a patient at a distance, typically several inches, from the first catheter assembly 10. When using a pair of catheter assemblies, blood is drawn through the second lumen 38 of one catheter assembly 10, runs through a hemodialysis machine, returns to the patient's vascular system through the second lumen 38 of the other catheter assembly 10.

The embodiments shown in FIGS. 1A, 1B, 1C, and 2 each have a slot 34. In embodiments having a slot 34, the length of the slot 34 in the tubular body 12 preferably corresponds to the distance that a person using the catheter assembly 10 desires to move the slidable member 24 in relation to the tubular body 12. This feature of the preferred embodiment may limit the movement of a sliding mechanism resting in the slot 34 and thereby limit the movement of the slidable member 24. This is advantageous because it ensures that the distal end 26 of the slidable member 24 will not slide too far distally. This may prevent accidental cutting or irritation to the vasculature of a hemodialysis patient. The limited length of the slot 34 also ensures that the slidable member 24 cannot be withdrawn too far in the proximal direction into the tubular body 12. It may be advantageous to keep the slidable member 24 within the first lumen 22 rather than withdrawing it entirely because the slidable member 24 provides support to the flexible walls of the tubular body 12. It may also be advantageous to limit the distance of the withdrawal of the slidable member 24 in the proximal direction because the slidable member 24 is more likely to cut the walls of the first lumen 22 of the tubular body 12 if it is withdrawn far inside the tubular body 12.

FIG. 11A shows another embodiment in which the slot 34 runs the entire length of the tubular body 12. In other embodiments, the slot 34 may run less than the entire length of the tubular body 12. FIG. 11B shows how the embodiment depicted in FIG. 11A has a slot 34 that is narrower than the diameter of the slidable member 24. This feature keeps the slidable member 24 inside the first lumen 22 while still allowing a user to access the slidable member 24 from the exterior of the tubular body 12. In embodiments having a slidable member 24 with an elongate center portion 30 that is not cylindrical, the slot 34 is preferably structured so that the slidable member 24 may not be removed laterally.

In addition to protecting the vasculature of a hemodialysis patient, the preferred embodiment reduces the risk of accidental pricking after the catheter assembly 10 is removed from a patient. Typically, dialysis needles are large and sharp. After dialysis is completed and the needles are removed from the patient, there is a risk that the patient or another person may be pricked by the needles. In the preferred embodiment, there is very little risk of accidental pricking because the distal end 26 of the sharp slidable member 24 is placed in the shielded position before the catheter assembly 10 is even withdrawn from the patient. Although this feature is particularly useful in the field of hemodialysis, it may be useful in other medical procedures as well.

As shown in FIGS. 1A, 1B, and 1C, the catheter assembly 10 may optionally include a hub 42. The catheter assembly 10 of FIGS. 1A, 1B, and 1C contains slot 34 to facilitate the sliding of the slidable member 24 similar to the slot 34 shown in FIG. 2. However, the slot 34 in FIGS. 1A, 1B, and 1C is concealed from the user's view by the hub 42. In the preferred embodiment, the hub 42 facilitates the sliding of the slidable member 24 between the exposed position and the shielded position. The preferred embodiment of the hub 42 includes three main components: a flare nut 44; a female luer lock adapter 46; and a male luer lock 48. The flare nut 44 preferably has a narrow distal end 92, a wide proximal end 50, and a central opening 52 that runs the length of the flare nut 44. The central opening 52 of the flare nut 44 is narrower at the narrow distal end 92 of the flare nut 44 and fits closely around the tubular body 12. The wide proximal end 50 of the flare nut 44 creates a wide central opening 52, which is lined with female threading 60. Like the flare nut 44, the female luer lock adapter 46 has a distal end 54, a proximal end 56, and a central opening 58 that runs the length of the female luer lock adapter 46. The central opening 58 of the female luer lock adapter 46 is slip-fit with the tubular body 12. The distal end 54 of the female luer lock adapter 46 fits within the wide central opening 52 at the proximal end 50 of the flare nut 44. In this preferred embodiment of a hub 42, the distal end of the female luer lock adapter 46 has male threading 62. The female threading 60 on the proximal end 50 of the flare nut 44 is capable of engaging the male threading 62 on the distal end 54 of the female luer lock adapter 46.

As shown in FIGS. 1A, 1B, and 1C, the flare nut 44 and the female luer lock adapter 46 of the preferred embodiment fit together such that there is a gap 64 between the distal end 54 of the female luer lock adapter 46 and the interior portion 66 of the flare nut 44. The length of this gap 64 corresponds to the size of the knob 36 or other sliding mechanism at the slidable member 24. The threading between the flare nut 44 and the female luer lock adapter 46 enables these two components of the hub 42 to be fitted around the knob 36 or other sliding mechanism at the proximal end 28 of the slidable member 24.

Like the flare nut 44, the female luer lock adapter 46 of the preferred embodiment has a central opening 58 that fits around the tubular body 12. The proximal end 56 of the female luer lock adapter 46 has a set of male threads 136. These male threads 136 extend proximally from the proximal end 56 of the female luer lock adapter 46 to the most proximal point of the female luer lock adapter 46. These luer threads 136 are capable of mating with a female luer thread 72 on the male luer lock adapter 48 located proximally to the female luer lock adapter 46.

The male luer lock adapter 48 forms the proximal portion of the hub 74. The male luer lock adapter 48 has a distal end 76, a proximal end 78, and a central opening 80 that fits closely around the tubular body 12. Unlike the flare nut 44 and the female luer lock adapter 46, the male luer lock adapter 48 is fixed to the tubular body 12. At the distal end of the male luer lock adapter 48, the male luer lock adapter 48 has a female luer thread 72 that fits with the male luer thread 136 on the female luer lock adapter 46. The male luer lock adapter 48 has a cavity 82 at the proximal end 78, which is continuous with the interior of the tubular body 12. The most proximal point 84 of the male luer lock adapter 48 preferably has a male luer thread 86 to facilitate the attachment of tubing or a syringe. Any mechanism for attaching tubing or a syringe known in the art may also be used instead of or in addition to a male luer thread 86.

FIGS. 1A and 1B illustrate that when the distal end 26 of the slidable member 24 of the preferred embodiment is in the exposed position, the male luer thread 136 of the female luer lock adapter 46 is not engaged with the female luer thread 72 of the male luer lock adapter 48. Further, the flare nut 44 is pushed forward so that the distal end 92 of the flare nut 44 contacts a stopping ring 88 on the exterior of the tubular body 12. The stopping ring 88 is disposed on the tubular body 12 so that when the sliding mechanism is at the most distal location 90 of the slot 34, the distal end 92 of the flare nut 44 is touching the stopping ring 88.

Once the tubular body 12 is inserted into a vascular access site, the user may rotate the flare nut 44 and the female luer lock adapter 46 so that the male luer thread 136 of the female luer lock adapter 46 engages the female luer thread 72 of the male luer lock adapter 48. Engaging the luer threads causes the knob 36 or other sliding mechanism at the proximal end 28 of the slidable member 24 to move proximally. This brings the distal end 26 of the slidable member 24 within the first lumen 22 and into the shielded position.

The components of the hub 42 of the preferred embodiment are preferably made from a clear plastic material. This enables a user to see that the components of the catheter assembly 10 are working correctly. It also enables a user to utilize the cavity 82 at the proximal end 78 of the male luer lock 48 as a flash chamber. A flash chamber allows a user to quickly confirm visually that a device has punctured a blood vessel by the presence of blood in the flash chamber. Although it is preferred that all of the component parts of the hub 42 be composed of a clear plastic material, other embodiments may have only one component part of the hub 42 that is made of a clear plastic material or no component parts that are made of clear plastic.

In the preferred embodiment of the hub 42, the proximal end of the first lumen 22 of the tubular body 12 is occupied by an obturation 134. The obturation 134 prevents fluids in cavity 82 from flowing in the distal direction through the proximal end of the first lumen 22. The obturation 134 may be a solid material. Alternatively, the obturation 134 may be made of filler glue or adhesive that serves to block the proximal end of the first lumen 22. In some embodiments, it may be preferable to have a long slidable member 24 with a sliding mechanism disposed near the middle. In these embodiments, the proximal end 28 of the slidable member 24 functions as an additional support for the tubular body 12. The obturation 134 in these embodiments may be shorter than in other embodiments in order to accommodate the long slidable member 22. The foregoing descriptions of possible obturations are exemplary only; any other obturation 134 known in the art may be used.

The luer lock hub 42 of the preferred embodiment is advantageous because luer locks are commonly used in medical devices and are thus familiar to medical personnel. However, other embodiments may have a syringe fastened to the proximal end 16 of the tubular body that operates as a hub 42. Any other hub 42 known in the art may be used. Further, a specialized hub 42 may be created using techniques known in the art. These and other variations of a hub 42 are possible. Still other embodiments may not have a hub 42 at all.

Many embodiments may utilize a seal or sealing surface to prevent the flow of blood proximally through the first lumen. The embodiments shown in FIGS. 1A, 1B, 1C, 2, 3A, 4A, 5A, 11A, 12, 13, 14, 15, 16, an 17, may employ a slip-fit between the exterior of the slidable member 24 and the interior of the first lumen 22. In addition, or in the alternative, a viscous biocompatible lubricant such as silicone or glycerin may be placed between the exterior of the slidable member 24 and the interior of the first lumen 22. The foregoing seals and sealing surfaces are exemplary only. Any seal or sealing surface known to a person of ordinary skill in the art may be used.

The solid slidable member 24 of the preferred embodiment of the catheter assembly 10 lends itself to a variety of useful configurations for puncturing tissue. In some embodiments, the elongate center portion 30 of the slidable member 24 is cylindrical. FIGS. 1A, 1B, 1C, 2, and 3A depict embodiments with a cylindrical elongate center portion 30 of the slidable member 24. In the embodiments shown in FIGS. 1A, 1B, 1C, 2, and 3A, the distal end 26 of the slidable member 24 may be a sharp beveled edge. In embodiments having a slidable member 24 with a sharp beveled edge 94, it is preferable that the tubular body 12 also have a beveled distal end 20 and that the beveling of the slidable member 24 parallel the beveling of the tubular body 12. It is also advantageous that the slidable member 24 be unable to rotate in relation to the tubular body 12. This keeps the beveling of the slidable member 24 parallel to the beveling of the tubular body 12 throughout the sliding of the slidable member 24 between the shielded position and the exposed position. If the slidable member 24 rotates as it is moved longitudinally within the first lumen 22, this may increase the risk of damaging a blood vessel, a fistula, or the inner lining of the first lumen 22 of the tubular body 12. Although these features are considered advantageous, embodiments without these features are also envisioned.

Figures 4A, 4B:
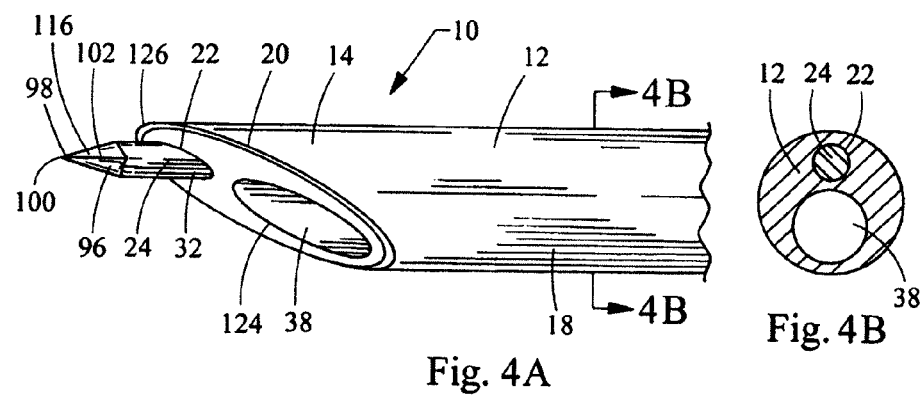
FIG. 4A is a partial a partial perspective view of a catheter assembly.
FIG. 4B is a cross-sectional view of the catheter assembly of FIG. 4A taken along line 4B-4B.

As shown in FIG. 4A, instead of a beveled edge 94, the distal end 26 of an slidable member 24 with a cylindrical elongate center portion 30 may have a plurality of faces 96 that come together at the most distal location 98 of the slidable member 24 to form a point 100. In some embodiments, like the one shown in FIG. 4A, the faces 96 may be triangular. In other embodiments, each face 96 forms a quadrilateral, a tear-drop shape, or a combination of several such shapes. The edge 102 between each pair of faces 96 provides a sharp cutting surface 116. The plurality of sharp edges may increase the cutting ability of the slidable member 24. The embodiment shown in FIG. 4A has three faces 96. However, the number of faces 96 may vary. Other embodiments may have four, five, or more faces. In some embodiments the faces 96 will not be flat, but rather they will be curved and in some embodiments may spiral toward a point 100 at the most distal location 98 of the slidable member 24.

Figures 3A, 3B:
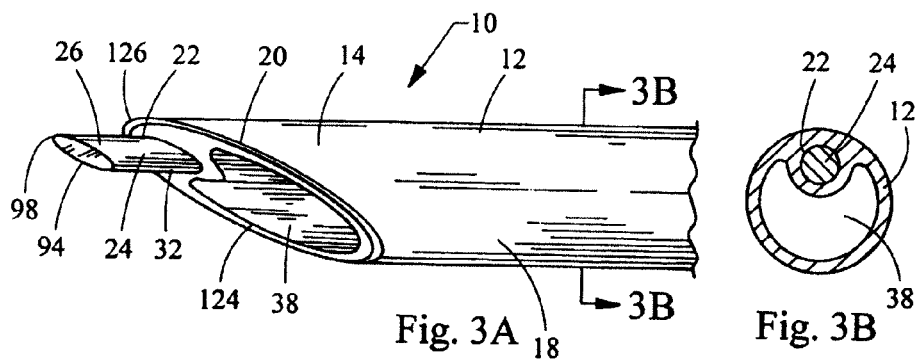
FIG. 3A is a partial perspective view of a catheter assembly.
FIG. 3B is a cross-sectional view of the catheter assembly of FIG. 3A taken along line 3B-3B.

As shown in FIGS. 3A, 3B, 4A, and 4B, in embodiments having a slidable member 24 with a cylindrical elongate center portion 30, the slidable member 24 will generally fit closely within a cylindrical first lumen 22. A fluid-tight fit may be facilitated by the use of a viscous biocompatible lubricant between the exterior of the slidable member 24 and the interior of the first lumen 22 of the tubular body 12. The second lumen 38 may have a non-circular cross-sectional shape. As shown in FIG. 3A, one possible non-circular cross-sectional shape is a crescent-like cross-sectional shape such that the second lumen 38 is wrapped around the first lumen 22. Alternatively, the second lumen 38 may have a circular cross-sectional shape as shown in FIG. 4A. The crescent-like cross-sectional shape may be advantageous for some uses because it maximizes the area of the second lumen 38, allowing for maximal blood flow. The circular cross-sectional shape shown in FIG. 4A may be advantageous for other uses. The circular cross-sectional shape may add greater strength to the tubular body 12. It also may reduce the risk of blood catching or clotting because there are no narrow portions of the second lumen 38. Likewise, the circular cross-sectional shape may be advantageous when the catheter assembly 10 is used to insert a guide wire because a guide wire is unlikely to catch on the circular second lumen 38.

Figures 5A, 5B:
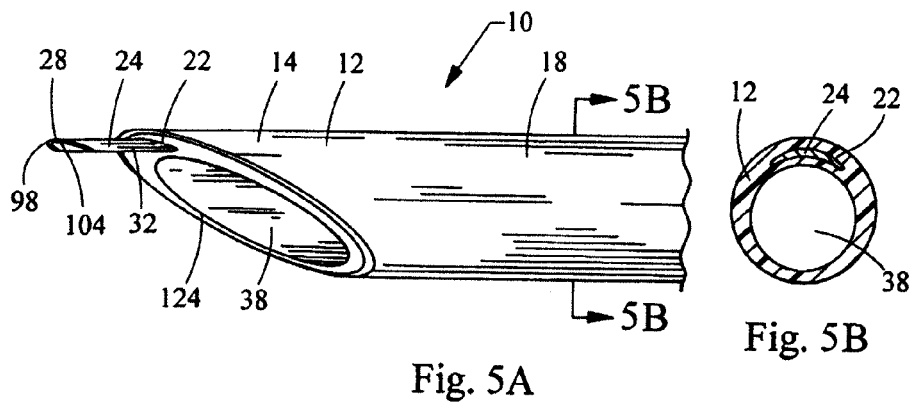
FIG. 5A is a partial perspective view of a catheter assembly.
FIG. 5B is a cross-sectional view of the catheter assembly of FIG. 5A taken along line 5B-5B.
Figures 6A, 6B:
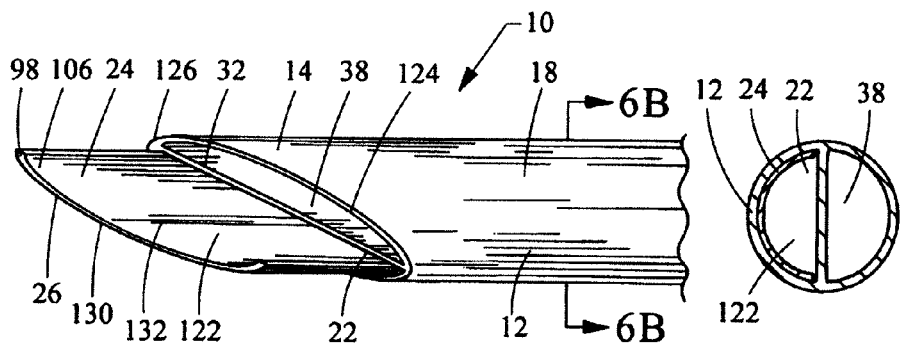
FIG. 6A is a partial perspective view of a catheter assembly.
FIG. 6B is a cross-sectional view of the catheter assembly of FIG. 6A taken along the line 6B-6B.
Figure 7:
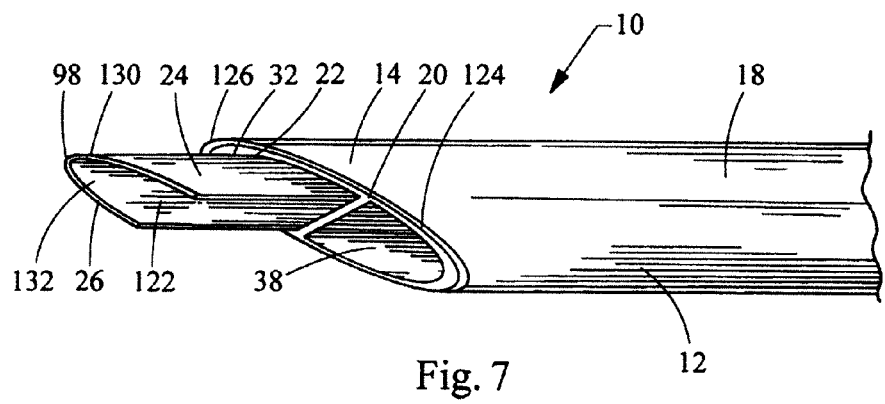
FIG. 7 is a partial perspective view of a catheter assembly.
Figure 8:
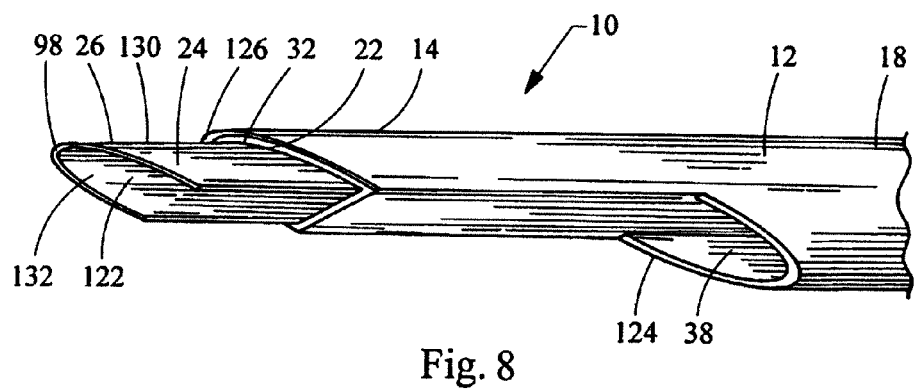
FIG. 8 is a partial perspective view of a catheter assembly.

As shown in FIGS. 5A, 5B, 6A, 6B, 7, 8, 9, and 10, the solid slidable member 24 may also have a curved shape. A curved slidable member 24 may have a sharp most distal location 98 at a central point 104 along the slidable member's curve as shown in FIGS. 5A, 7 and 8, two sharp most distal locations 98 at each end of the slidable member's curve as shown in FIG. 10, or a sharp most distal location 98 at one end 106 of the slidable member's curve as shown in FIGS. 6A and 9. The foregoing variations of a curved slidable member 24 are exemplary. Other variations of a curved slidable member 24 known to a person of ordinary skill in the art are also envisioned.

Curved slidable members lend themselves to a variety of useful features. In some embodiments, such as those shown in FIGS. 5A and 5B, a curved slidable member 24 can be fitted closely into a curved first lumen 22. This allows the second lumen 38 to have a circular cross-sectional shape. The circular cross-sectional shape of the second lumen 38 may be advantageous because it may allow for a high volume of blood flow, minimize the risk of cells catching in crevices or clotting, provide more strength than a crescent-shaped second lumen 38, and allow for devices, such as guide wires, to be easily pushed through the second lumen 38. FIG. 6A illustrates another embodiment with a curved slidable member, which has a second lumen 38 with a non-circular cross-sectional shape.

Figure 12:
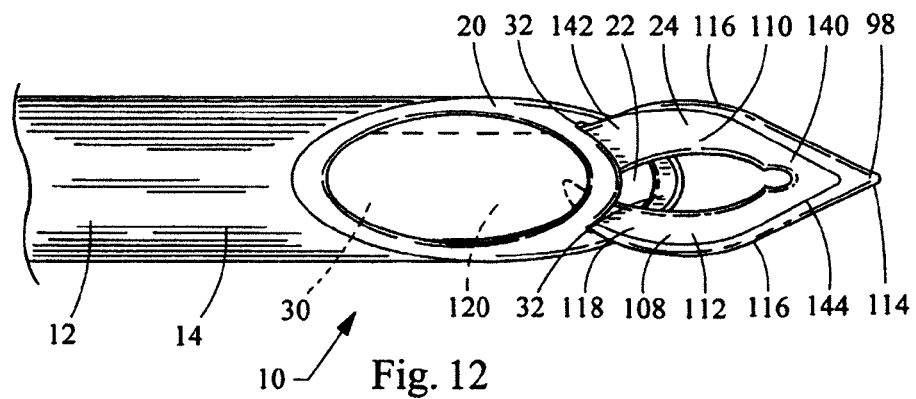
FIG. 12 is a partial perspective view of an catheter assembly having an expandable tip in the exposed position.
Figure 13:
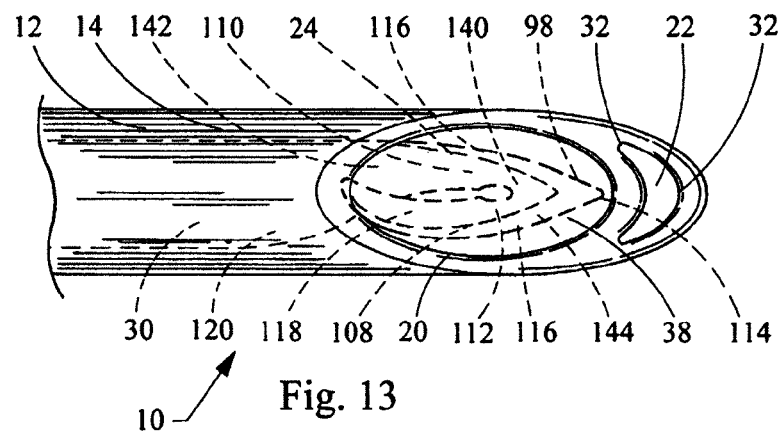
FIG. 13 is a partial perspective view of a catheter assembly having an expandable tip in the shielded position.
Figure 14:
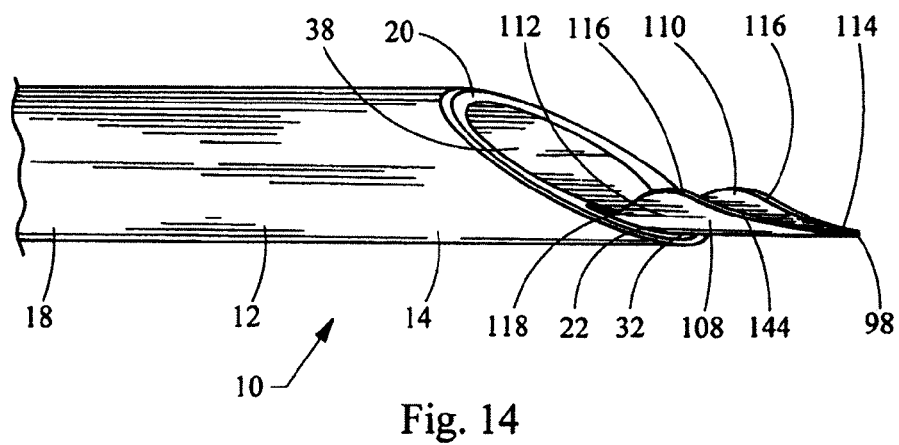
FIG. 14 is a partial perspective view of an catheter assembly with an expandable tip.
Figure 15:
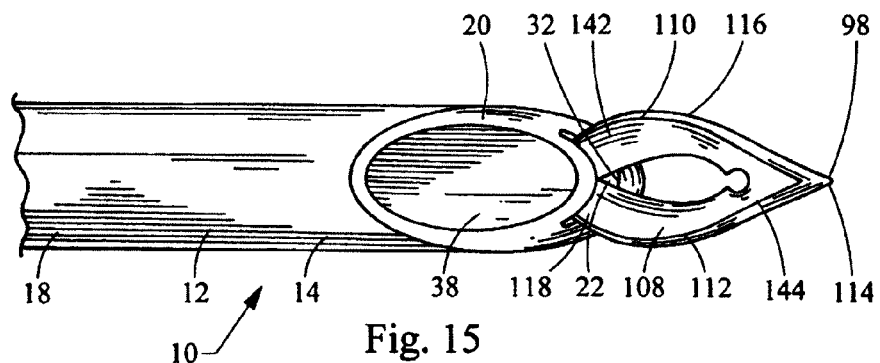
FIG. 15 is a partial perspective view of a catheter assembly with an expandable tip.

As shown in FIGS. 12, 13, 14, 15, and 16, a curved slidable member 24 may have an expandable slidable member tip 108. The expandable slidable member tip 108 is attached to the distal end 120 of the elongate center portion 30 of the slidable member 24. The tip 108 has a first leg 110 and a second leg 112. The first leg 110 has a distal end 140 and a proximal end 142. Likewise, the second leg 112 has a distal end 144 and a proximal end 118. The proximal end 142 of the first leg 110 is attached to the distal end 120 of the elongate center portion 30 of the slidable member 24 and extends distally to the most distal location 98 of the slidable member 24. At the most distal location 98 of the slidable member 24, the distal end 140 of the first leg 110 and the distal end 144 of the second leg 112 come together in this embodiment to form sharp end point 114. The distal end 144 of the second leg 112 is attached to the most distal location 98 of the slidable member 24. The second leg 112 extends proximally from the most distal location 98 of the slidable member 24. In some embodiments, the second leg 112 is curved to form a cutting surface 116. In other embodiments, both the first leg 110 and the second leg 112 are curved to form two cutting surfaces. The proximal end 118 of the second leg 112 may be attached to the distal end 120 of the elongate center portion 30 of the slidable member 24 as shown in FIG. 15. Alternatively, the proximal end 118 of the second leg 112 may be loose as shown in FIG. 12. Embodiments having an expandable slidable member tip 108 may be advantageous because they allow the user to create a cutting surface 116 that has a greater width than the width of the first lumen 22.

FIGS. 12 and 13 each show an embodiment having an expandable slidable member tip 108 with two curved legs. The embodiment shown in each figure also has a loose second leg 112. When the slidable member 24 is in the shielded position, as shown in FIG. 13, the first leg 110 and loose second leg 112 will be compressed together to fit within the first lumen 22. As the slidable member 24 is pushed in the distal direction and the expandable slidable member tip 108 begins to protrude beyond the distal end 32 of the first lumen 22, the first leg 110 and the loose second leg 112 will become partially free of the first lumen 22 as shown in FIG. 12. Once partially free of the first lumen 22, the legs expand laterally as shown in FIG. 12 to increase the width of the cutting surface 116. It is preferable, however, in the embodiment having a loose second leg 112 that the slidable member 24 not be extended so far distally that the proximal end 118 of the second leg 112 is located distally from the distal end 32 of the first lumen 22. This prevents the proximal end 118 of the loose second leg 112 from catching on the distal end 14 of the tubular body 12 when the user attempts to slide the expandable slidable member tip 108 back into the first lumen 22.

Figure 16:
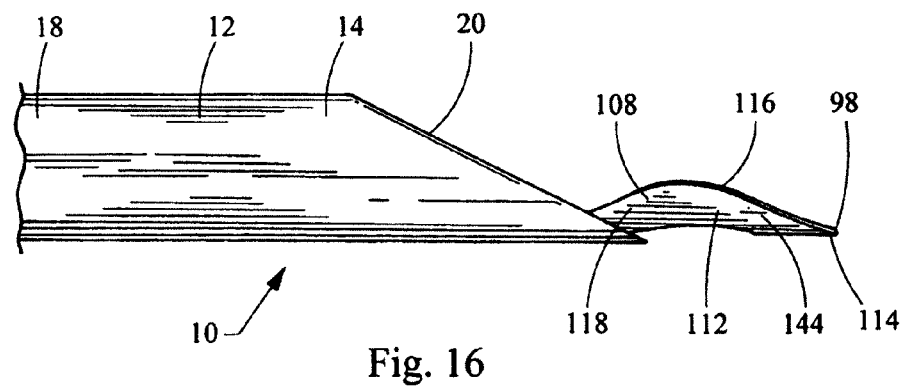
FIG. 16 is a partial side elevation view of the catheter assembly of FIG. 15.

FIGS. 14, 15, and 16 show an embodiment in which the slidable member has an expandable tip 108 with a second leg 112 attached to the distal end 120 of the elongate center portion 30 of the slidable member 24. In this embodiment, the two legs are compressed together when the slidable member 24 is withdrawn into the first lumen 22. As the slidable member 24 is moved distally and the legs become free of the first lumen 22, they expand laterally to increase the width of the cutting surface 116. In this embodiment, the slidable member 24 may move distally so that the proximal end 118 of the attached second leg 112 is located distally in relation to the distal end 14 of the tubular body 12. The second leg 112 will not snag on the distal end 14 of the tubular body 12 when the slidable member 24 is drawn back inside the first lumen 22 because the proximal end 118 of the second leg 112 is attached to the distal end 120 of the elongate center portion 30 of the slidable member 24.

As shown in FIGS. 6A, 7, 8, 9, and 10, some embodiments of the catheter assembly 10 may pair a curved slidable member 24 with a first lumen 22 that does not closely fit around the entirety of the curved slidable member 24. The possible variations of the curved slidable member's cross-sectional shape include, but are not limited to, a half-round shape as shown in FIGS. 7, 8, and 10, or a quarter-round shape as shown in FIGS. 6A and 9. The curved slidable member 24 generally fits tightly against the first lumen 22 along the convex side 130 of the slidable member's curve. A slip-fit or a viscous biocompatible sealing surface may be used to insure a tight fit between the convex side 130 of the slidable member 24 and the interior of the first lumen 22. The first lumen 22 is open along the concave side 132 of the slidable member 24 to create a longitudinal opening 122. This longitudinal opening 122 in the first lumen 22 may be used to transfer fluids or to pass a guide wire.

A catheter assembly 10 having a first lumen 22 with a longitudinal opening 122 is particularly useful for performing hemodialysis. Blood may be drawn through one lumen of the catheter assembly 10 and brought back via the other lumen of the catheter assembly 10. In these embodiments, the area of the longitudinal opening 122 in the first lumen 22 is preferably similar to the area of the second lumen 38 in order to ensure that a roughly consistent amount of blood is being returned to the patient's vascular system as the blood being removed from the patient's vascular system. Embodiments having a longitudinal opening 122 in the first lumen 22 are particularly advantageous in hemodialysis because they allow for the use of only one vascular access site. This reduces the number of punctures that must be made per hemodialysis session, thereby reducing the risk of damage to the blood vessel or fistula.

In some embodiments with a longitudinal opening 122, the distal end 32 of the first lumen 22 and the distal end 124 of the second lumen 38 will run together to form a single distal end 14 of the tubular body 12. As shown in FIGS. 6A and 7, this distal end 14 of the tubular body 12 may be beveled. As shown in FIGS. 8, 9, and 10, in other embodiments having a longitudinal opening 122 in the first lumen 22, the first lumen 22 and the second lumen 38 will have distal ends that do not run together. In these embodiments, the distal end 32 of the first lumen 22 will be located distally in relation to the distal end 124 of the second lumen 38. It may be advantageous to have lumens located at a distance from one another because this allows for blood to be drawn from one location in the vascular system and returned at a second location. This prevents the catheter assembly 10 from drawing blood that has already been filtered and returned to the body, thereby increasing the efficiency of hemodialysis.

In many embodiments the distal end 14 of the tubular body 12 is beveled as shown in FIGS. 1A, 1B, 1C, 2, 3A, 4A, 5A, 7, 11A, 12, 13, 14, 15, and 16. The beveling of the distal end 14 of the tubular body 12 is generally such that the most distal location 126 of the distal end 14 of the tubular body 12 is at the most distal point of the distal end 32 of the first lumen 22. The beveled edge 20 of the tubular body 12 allows the tubular body 12 to easily push through an incision made by the distal end 26 of the slidable member 24. As shown in FIGS. 1B and 1C, it is also preferable that the most distal location 126 of the beveled distal end 14 of the tubular body 12 be slightly tapered toward the distal end 32 of the first lumen 22, thereby creating a backward bevel 146. This backward bevel 146 helps the tubular body 12 to easily follow the slidable member 24 into an incision site.

Figure 17:
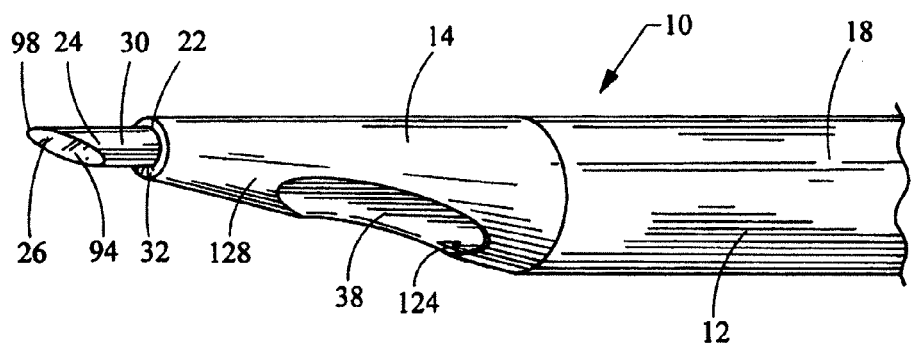
FIG. 17 is a partial perspective view of a catheter assembly.

FIG. 17 shows an embodiment in which the tubular body 12 has a tapered distal end 128. In this embodiment, the distal end 14 of the tubular body 12 is narrowest at the distal end 32 of the first lumen 22. The distal end 124 of the second lumen 38 forms an opening in the tapered distal end 128 of the tubular body 12. The distal end 124 of the second lumen 38 is located proximally in relation to the distal end 32 of the first lumen 22. The tapered distal end 128 of the tubular body 12 may be paired with a slidable member 24 having a cylindrical elongate center portion 30 as shown in FIG. 17. Alternatively, the tapered distal end 128 of the tubular body 12 may be paired with a curved slidable member 24 having a non-circular cross-sectional shape. One possible non-circular cross-sectional shape is a crescent-like cross-sectional shape. In embodiments having a tubular body 12 with a tapered distal end 128, the sharp distal end 26 of the slidable member 24 may be used to cut the skin and puncture the blood vessel. As the sharp distal end 26 of the slidable member 24 is pushed into the incision, the tapered distal end 128 of the tubular body 12 allows the tubular body 12 to easily follow the sharp slidable member 24 into the incision without further ripping or tearing the tissue of the patient.

The tubular body 12 of the catheter assembly 10 is preferably made of a flexible biocompatible material such as an elastomer or a plastic. Suitable materials include, but are not limited to, polyurethanes, polyethelene, PTFE, silicones, polyolefin, polyesters, and polyimides. The biocompatible materials listed are included for exemplary purposes and are not meant to be limiting. Any other biocompatible material known to a person of ordinary skill in the art may be used. Additionally, combinations of multiple biocompatible materials may also be used in a single catheter assembly 10. Flexible biocompatible materials are advantageous because they have sufficient integrity to withstand the force applied to them when the catheter assembly 10 is inserted into a patient, but are also sufficiently flexible that they are unlikely to cut or tear the patient's tissue.

The slidable member 24 is preferably made of a hard biocompatible material such as a metal, plastic, a fiber-reinforced plastic, or a combination thereof. In embodiments having an expandable slidable member tip 108, the slidable member 24 is preferably composed of an elastic or superelastic material, a rigid plastic, or a combination thereof. Any other material or combination of materials known to a person of ordinary skill in the art may be used for the slidable member 24. Because the slidable member 24 in many embodiments is composed, at least in part, of a hard material it provides support to the flexible tubular body 12. This allows the catheter assembly 10 to be inserted into a patient without causing the tubular body 12 to collapse. Embodiments having a curved slidable member 24 such as a slidable member 24 with a crescent-like cross-sectional shape may be flexible in the lateral direction, allowing the catheter assembly 10 to bend laterally as needed during use, but have rigidity in the longitudinal direction, preventing the tubular body 12 from collapsing during insertion. This feature of some of the embodiments of the catheter assembly 10 may be useful when the catheter assembly 10 must be pushed through the vascular system. The tubular body 12 will bend in the lateral direction with the vasculature as needed, but the integrity of the second lumen 38 will be maintained.

The preferred embodiment of a catheter assembly 10 may be useful for inserting guide wires into a lumen in a body. A guide wire may be pushed through the second lumen 38 of the catheter assembly. Alternatively, in embodiments having a longitudinal opening 122 in the first lumen 22 of the catheter assembly 10, a guide wire may be pushed through the longitudinal opening 122. This may be advantageous because the second lumen 38 may be used for other purposes such as drawing blood or inserting blood while the guide wire is being inserted.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A catheter assembly comprising:
    a catheter having a distal end and a proximal end;
    a lumen running longitudinally from said distal end of said catheter to said proximal end of said catheter; and
    a solid slidable member disposed within said lumen, said slidable member having an elongate center portion, said elongate center portion having a proximal end and a distal end, said slidable member being adapted to slide within said first lumen;
    an expandable tip attached to said distal end of said elongate center portion of said slidable member, said tip of said slidable member comprising a first leg and a second leg connected together a distal end of said expandable tip, wherein said first leg extends from said distal end of said elongate center portion to a most distal location of said slidable member and said second leg is attached to said most distal location and extends proximally therefrom, said second leg being curved and forming a cutting surface along an outer edge, said outer edge of said cutting surface abutting an inner surface of said catheter forming said lumen in a retracted position, said outer edge being capable of cutting skin, wherein a lateral width of said cutting surface of said expandable tip in an expanded state is wider than a lateral width of said lumen, and wherein said second leg engages said opening of said lumen when said slidable member is retracted within said lumen, thereby compressing said second leg to permit said expandable tip of said slidable member to be withdrawn into said lumen.

2. The catheter assembly according to claim 1, wherein said second leg has a distal end and a proximal end and said proximal end of said second leg is connected to said distal end of said elongate center portion of said slidable member.

3. The catheter assembly according to claim 1, wherein said second leg has a distal end and a proximal end and said proximal end of said second leg is unconnected to said elongate center portion of said slidable member.

* * * * *